United States Patent [19]

Ciborowski et al.

[11] 4,071,561
[45] Jan. 31, 1978

[54] METHOD OF PREVENTION OF DISTURBANCES AND/OR EFFECTS OF DISTURBANCES IN THE REACTION SYSTEM OF OXIDATION OF HYDROCARBONS IN A LIQUID PHASE UNDER PRESSURE WITH GASES CONTAINING OXYGEN

[75] Inventors: Stanislaw Ciborowski, Warsaw; Zbigniew Szczypinski, Tarnow; Kazimierz Balcerzak; Andrzej Jaworski, both of Warsaw; Andrzej Kasznia; Andrzej Krzysztoforski, both of Tarnow; Stanislaw Kurowski, Warsaw; Jan Redzi; Józef Szparski, both of Tarnow, all of Poland

[73] Assignee: Zaklady Azotowe im. F. Dzierzinskiego, Tarnow, Poland

[21] Appl. No.: 621,530

[22] Filed: Oct. 10, 1975

[30] Foreign Application Priority Data

Oct. 12, 1974 Poland .................................. 174794

[51] Int. Cl.$^2$ ...................... C07C 27/12; C07C 29/00; C07C 45/02; C07C 51/33
[52] U.S. Cl. .......................... 260/586 P; 260/524 R; 260/610 B; 260/621 C; 260/631 R; 260/687 R; 260/700
[58] Field of Search ........... 260/586 P, 524 R, 621 C, 260/610 B, 631 R, 687 R, 700

[56] References Cited
PUBLICATIONS

"Chemical Engineer's Handbook," Perry, editor, McGraw Hill Book Co., pp. 24–90, 1963.
"Encyclopedia of Chem. Tech.," vol. 9, pp. 295, 297, Kirk–Othmar (1966).

*Primary Examiner*—Norman Morgenstern
*Attorney, Agent, or Firm*—Eric P. Schellin

[57] ABSTRACT

Method for preventing disturbances in hydrocarbon oxidation reaction systems by rapid lowering of the temperature and/or pressure in the reaction system by means of intensive introduction of water into the system.

5 Claims, No Drawings

METHOD OF PREVENTION OF DISTURBANCES AND/OR EFFECTS OF DISTURBANCES IN THE REACTION SYSTEM OF OXIDATION OF HYDROCARBONS IN A LIQUID PHASE UNDER PRESSURE WITH GASES CONTAINING OXYGEN

The present invention relates to a method for preventing disturbances and the effects of disturbances in a reaction system for oxidizing hydrocarbons in a liquid phase under pressure with gases containing oxygen.

Processes for oxidizing hydrocarbons in a liquid phase under pressure with gases containing oxygen are widely spread in industrial practice. Included among these processes are the following: oxidation of cyclohexane to cyclohexanol and cyclohexanone, oxidation of cumene to cumene hydroperoxide to produce phenol, oxidation of p-xylene to terephthalic acid, etc.

All of these processes are operated on a large industrial scale in processing lines with production capacities of thousands of tons per year. In the reaction systems of large lines there exist many hundreds of tons of flammable and explosive substances. This provides many hazards, of which two are of particular importance. The first of these, illustrated below with an example of a process for oxidizing cyclohexane, results from the possibility of a sudden escape outwards of large amounts of volatile vapors in the event of a large leak.

The process for oxidizing cyclohexane takes place at a temperature higher than the boiling point of cyclohexane under atmospheric pressure. Usually it occurs at a temperature of 150° C. to 160° C. at a pressure on the order of eight atmospheres, whereas the boiling point of cyclohexane at atmospheric pressure is only 80° C. Thus, in the event of any leaks in the reaction system with an accompanying pressure drop, the liquid cyclohexane within the reaction system, overheated in relation to the atmospheric pressure, is subject to intensive adiabatic evaporation.

The result of balance calculations for conditions mentioned above is that, in a case of a pressure drop in the reaction system from eight atmospheres to atmospheric pressure, the thermal equilibrium will be restored only after evaporation of about 50% of the cyclohexane. At this state, the temperature of the remaining cyclohexane will drop to about 80° C., i.e., to the boiling point at atmospheric pressure.

Taking into consideration that, in the reaction system of a cyclohexane oxidation plant with a capacity of 25,000 tons cyclohexanol and cyclohexanone per year, there is provided about 70 tons of cyclohexane, it may be feared in an extreme case that the occurrence of a large leak (e.g., breakdown of a pipe line of a large diameter) in the absence of precautionary means, about 35 tons of cyclohexane vapors may escape from the apparatus.

The following table gives the amount of vaporous cyclohexane that can escape from the apparatus through a leak equalling the orifices of various diameters, upon the assumption of a critical outflow speed and of three different pressures and their corresponding temperatures. With the escape of vapors from the apparatus, the pressure and the temperature therein will drop.

| Orifice dia. /mm/ | Outflow rate of cyclohexane vapors t/min. | | |
|---|---|---|---|
| | p = 8 at t = 155° C | p = 5 at t = 152° C | p = 2 at t = 121° C |
| 25 | 0.074 | 0.050 | 0.027 |
| 50 | 0.292 | 0.200 | 0.103 |
| 100 | 1.170 | 0.800 | 0.415 |
| 250 | 7.27 | 5.00 | 2.58 |
| 500 | 29.2 | 20.0 | 10.4 |

It is evident that a considerable amount of cyclohexane vapors may escape from the apparatus very quickly. The resulting fog of flammable vapors has an enormous explosive force, and in the presence of an ignition source it may be the cause of a catastrophic explosion. Such a catastrophe, in a cyclohexane oxidation plant, has been described in *European Chemical News*, July 6, 1974.

The other kind of hazard accompanying the operation of processes of oxidation of hydrocarbons in a liquid phase with oxygen-containing gases is connected with the explosive properties of organic hydroperoxides taking part in these processes as intermediates or end products.

The hazards accompanying the explosive decomposition of hydroperoxides can be illustrated in the oxidation of cumene. In this process, the cumene is oxidized to cumene hydroperoxide. The raw oxidation product contains above 20% of the hydroperoxide.

The process is usually conducted at a temperature of 105° C. to 115° C., while at a somewhat higher temperature the cumene hydroperoxide decomposes in a highly exothermal way. The overheating of the reaction system causes an increase in the decomposition speed of the cumene hydroperoxide. A quicker decomposition results in a further temperature increase.

The reaction system is generally refrigerated with cooling water by means of heat exchangers either provided directly to the liquid to be oxidized, or situated outside and supplied by pumps. Although these heat exchangers can dissipate a definite amount of heat, beginning with a certain temperature characteristic of a reaction system, the heat exchangers are not sufficient to stop the temperature increase, leading to a catastrophic explosive decomposition of cumene hydroperoxide.

Although the reaction systems for cumene oxidation are designed in such a way that in the normal course of the process a possibility of heat extraction is foreseen, a disturbance may arise in the process which necessitates a rapid extraction of very great amounts of heat, which extraction cannot be handled by means of conventional membrane (diaphragm) heat exchangers.

An example of such a disturbance is the penetration in the reaction system of even a small amount of a substance which may calatyze the decomposition of cumene hydroperoxide. In such a case, the temperature of the reaction system rapidly increases beyond the capacity of a conventional heat exchanger.

Means for preventing the above-described hazards in industrial processes for oxidizing liquid hydrocarbons in a liquid phase under pressure are unknown at the present state of the art of engineering. At present, due to difficulties of a technical nature, only partial solutions are employed, which can only reduce a disturbance. In the process of oxidizing cyclohexane, where the hazard is the escape from the reaction system of vapors which form an explosive mixture with air, one of the safety precations is the sectioning of the installation. In the event of a leak, a system of rapidly closing dampers, controlled manually or automatically, divides the system into sections, thus limiting the amount of cyclohexane vapors which may escape to the atmosphere. This solution does not wholly eliminate the hazard, but only reduces its degree.

Another precautionary means consists of the construction of a system of drain tanks, into which the system can be evacuated in the event of a leak. However, this system has serious drawbacks. First of all, the speed of emptying, which may be a decisive factor in controlling the effects of a disturbance, is limited by the flow capacity of the draining pipe lines. In particular, because of the pressure reduction in such pipe lines, evaporation of cyclohexane occurs, which greatly increases its volume. Secondly, the drain tanks should have been provided with reflux condensers with a greater surface used for condensation of vapors formed from adiabatic evaporation. This would involve high costs, since the oxidation processes of organic compounds result in the formation of, among other things, acids, both the tanks and the reflux condensers must be made of corrosion-proof materials.

Since in most cases the pressurized oxidation system is connected with a pressureless system for the distribution of oxidation products, an emergency expansion of the contents of the pressurized system into the pressureless system can take place, causing a drop of both temperature and pressure in the pressurized system.

This method is more economical with regard to investment costs than the method of expansion into special drain tanks. However, the drawback of this method is, generally, a considerable limitation of the expansion speed, resulting from the volume, cooling surface, and similar physical properties of the pressureless distribution system.

There are also known methods of expansion of pressure systems through torches. However, the introduction of a flame into the system carries with it a new hazard. Also in this case there is a quantitative barrier limiting the speed of intervention, resulting from the flow capacity of the torch and the necessity of ensuring quick combustion.

It is thus evident that all of the known methods for reducing the hazards of leaks in the reaction pressure system have drawbacks which considerably limit their efficiency. The basic defect is a long operation period which, depending on the character and the size of the plant, amounts from a few to many dozens of minutes. With disturbances of greater extent, resulting from large leaks or considerable overheatings, these methods may fail completely.

With regard to processes for oxidizing cumene, where the hazard is accompanied by a possibility of a vigorous decomposition of hydroperoxides with development of greater amounts of heat, effective methods of controlling the emergency temperature increase are neither known nor applied. The only practically employed method is the construction of membrane cooling surfaces, the efficiency of which is limited.

SUMMARY OF THE INVENTION

The method according to the present invention provides a solution for the above-described problems, permitting a very rapid and effective prevention of the escape of hydrocarbon vapors through leaks occurring in the reaction system or controlling an uncontrolled increase of temperature due to the decomposition of hydroperoxides.

The essential feature of the method according to the present invention is a rapid lowering of the pressure and/or temperature in the reaction system by the intensive introduction of cold water into the interior of this system. The application of the present method is accompanied by considerable technical difficulties, as the oxidized hydrocarbons do not mix with water and form with it heteroazeotropic systems. These heteroazeotropic systems are characterized by a higher pressure of vapors, approximately equalling the sum of the hydrocarbon pressure and the water pressure at a given temperature, independent of the mutual quantitative ratio of these two media.

For example, the pressure of cyclohexane vapors at 150° C. is 5.67 atmospheres, while the pressure of vapors of the heteroazeotrope cyclohexane-water at the same temperature is 10.52 atmospheres. Thus, the introduction of water to the hot hydrocarbon, as a rule, causes a quick evaporation of its heteroazeotropes and an increase of pressure in the closed system, having an effect opposite to the desired one, and increasing the rate of escape of vapors through the leak.

Unexpectedly, it turned out that by a proper choice of the speed of introduction of water into the system and an appropriate method of its introduction, a rapid cooling of the hydrocarbon to the oxidized could be obtained, thereby avoiding a momentous essential pressure increase.

In the tests, various speeds of water introduction into the system and various methods of its introduction have been employed. Water was introduced either upon the surface of the hydrocarbon by a spray system, or beneath the surface of the hydrocarbon air inflow (through a system of bubblers, or through separate nozzles) by fluid streams, causing a thorough mixing of water and hydrocarbon.

As a criterion, such an amount of water has been assumed to be necessary for producing a temperature of hydrocarbon 5° C. lower than the boiling point of its hydroazeotrope under atmospheric pressure.

It has been discovered that if this amount of water is injected into the reactor in a short time, e.g., within 0.5 to 5 minutes, and if the injection of water is effected primarily on the surface of the hydrocarbon, a rapid cooling of the hydrocarbon can be reached, without a temporary pressure increase.

The mechanism of the operation can be elucidated in the following way. The first charge of cold water falling on the surface of the hydrocarbon causes a vigorous evaporation of its hydroazeotrope, with a drop of temperature in the boiling medium. However, the following charges of water injected quickly cause a condensation of the evaporated hydroazeotrope. Thus, an intensive water stream directed from the top clamps the phenomenon of the evaporation of the heteroazeotrope. At the same time, water falls gradually to the bottom of the reactor with intensive heat exchange without need for a diaphragm heat exchanger.

After the system has been brought to a temperature lower than the boiling point of the heteroazeotrope under atmospheric pressure, the system can be regarded as safe, especially when the leak in the system has been located above the level of the hydrocarbon.

A certain amount of inert materials contained in the reaction system (mostly gases remaining after consumption of oxygen in the reaction; in the case of hydrocarbon, mainly nitrogen) flow off from the system through the leak or with waste gases. The pressure in the system will thus be practically equal to the pressure of heteroazeotrope vapors, and in the case of the temperature's falling below the boiling point at atmospheric pressure, the cause of the escape of the hydrocarbon vapors to outside the system will disappear.

Injection of water into the reactor should be accompanied by simultaneous stopping of the inflow of the oxidizing gas, as well as the inflow of the hydrocarbon to be oxidized.

An additional positive effect of the application of the method according to the present invention is the fact that, after injection of water, liquid or vaporous mixtures of cyclohexane with water, rather than solely cyclohexane, will escape through the leak, regardless of the conditions, whether the leak is located on the fluid or on the vapors. The likelihood of an explosion after the cyclohexane has been diluted with water is much less.

With reference to the processes, wherein the purpose of cooling is the arrest of uncontrolled decomposition of hydroperoxides, it has been established that the cooling of the hydrocarbon to a temperature lower than the boiling point of its hydroazeotrope under atmospheric pressure will always be sufficient for stopping uncontrolled decomposition. It has been stated that an advantageous technical solution of the injection of water onto the surface of the hydrocarbon is the uniform introduction of water onto the entire hydrocarbon surface by a system of perforated and slotted sprinklers.

Depending on the character of the plant and the needs, water can be injected either to the reactor and/or to other apparatus in the pressure reaction system, e.g., used for the exchange of heat and mass between the waste gases and the incoming hydrocarbon, for separation of water, etc. The situation will depend, among other things, whether sectioning of the installation is used simultaneously with the injection of water.

The water source would most advantageously be a carbon steel tank (ball shaped) of the hydrophore type, in which constant pressure would be maintained by the pressure of nitrogen or air from the network.

Since water, generally, is detrimented to the processes for oxidizing hydrocarbons, its casual penetration into the reaction system should be prevented. The most advantageous way of preventing this is by cutting off the inflow of water to the reactor by means of two remotely controlled dampers between which a control valve of small diameter would permanently be kept in an open position. To avoid the introduction of gases into the reaction system, the dampers should be closed automatically when the water level reaches its minimum.

The method of the present invention is illustrated below by means of two examples. The first example relates to the oxidation of cyclohexane; the second, to the oxidation of cumene. These examples do not limit in any way the scope of the invention.

EXAMPLE I

Fifty tons of cyclohexane at a temperature of 155° C. and a pressure of 7.3 atmospheres are contained in a reactor for cyclohexane oxidation having a capacity of 110m$^3$. Fifty m$^3$ of water at 15° C. was introduced into the reactor above the surface of the cyclohexane within two minutes from a water tank having a capacity of 70m$^3$, under a pressure of 16 atmospheres.

The temperature in the reactor dropped to 65° C., and the pressure in the reactor after simultaneous removal from the system of inerts with waste gases dropped to atmospheric pressure.

EXAMPLE II

A reactor for the oxidation of cumene having a capacity of 300m$^3$ contained 150 tons of oxidation products comprising 25% by weight of cumene hydroperoxide, byproducts such a acetophenone, dimethylphenylcarbinol, and the like, and the remainder cumene. When the temperature of this mixture of oxidation products increased to 130° C., 55 tons of water at 25° C. was introduced into the system within three minutes.

The temperature of the liquid in the reaction system dropped to 90° C., a safe value, at which temperature the thermal decomposition of cumene hydroperoxide is so slow that the temperature of the liquid can be controlled by means of watercooled heat exchangers installed in the system.

We claim:

1. A method for the prevention of disturbances and effects of disturbances in a reaction system for the oxidation of hydrocarbons in the liquid phase under pressure with oxygen containing gases which comprises lowering in the system, the temperature and pressure in the reactor and/or other apparatus of the reaction system by introduction of water in an intensive way at a rate and volume sufficient to lower the temperature of the hydrocarbon to at least 5° C. lower than the boiling point of its hydroazeotrope under atmospheric pressure, or to a temperature at which there does not occur an uncontrolled decomposition of hydroperoxides, while simultaneously preventing a momentary pressure increases due to hydroazeotrope evaporation.

2. The method of claim 1 characterized in that water is introduced primarily from above onto the surface of the hydrocarbon in a uniform way by means of perforated or slotted sprinklers provided with splash elements mounted below.

3. The method of claim 1 characterized in that the amount of water necessary for lowering the temperatures to the required level is introduced within 0.5 to 5 minutes.

4. The method of claim 1 wherein the hydrocarbon is cumene.

5. The method of claim 1 wherein the hydrocarbon is cyclohexane.

* * * * *